United States Patent [19]
Hoffmann et al.

[11] Patent Number: 5,902,329
[45] Date of Patent: May 11, 1999

[54] EXPLANTABLE LEAD

[75] Inventors: Drew A. Hoffmann, Los Gatos; Dean F. Carson, Mountain View, both of Calif.

[73] Assignee: Pacesetter, Inc., Sunnyvale, Calif.

[21] Appl. No.: 08/970,492

[22] Filed: Nov. 14, 1997

[51] Int. Cl.⁶ .................................................. N61N 1/05
[52] U.S. Cl. ............................................................ 607/121
[58] Field of Search .................... 607/116, 119, 607/120, 121, 122, 123

[56] References Cited

U.S. PATENT DOCUMENTS 5,324,324  6/1994  Vachon et al. .......................... 607/120
5,713,493  2/1998  Lindegren ............................... 607/116

Primary Examiner—William E. Kamm
Attorney, Agent, or Firm—Steven M. Mitchell

[57] ABSTRACT

An extractable lead and method for chronic blood contacting use. The new lead contains a hydrogel coating having a thickness increase greater than 10% when hydrated. A thick coating is used to provide a shear layer so that the coating tears during extraction, either at the coating/lead interface, between layers of the coating itself, or at the coating/tissue interface. Furthermore, because of the flexibility of such a thick coating, contracture of any fibrous capsule that may have formed is not a problem during extraction, since instead of contracting onto the lead, it contracts onto the flexible coating which can be extracted out of the tight capsule.

20 Claims, 12 Drawing Sheets

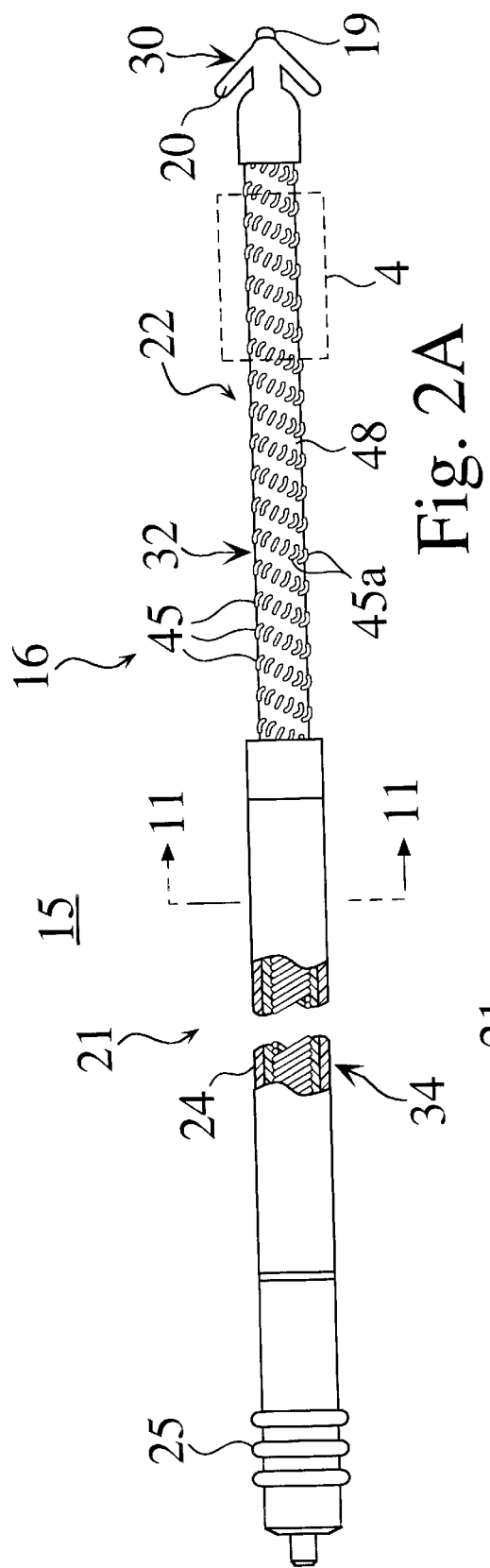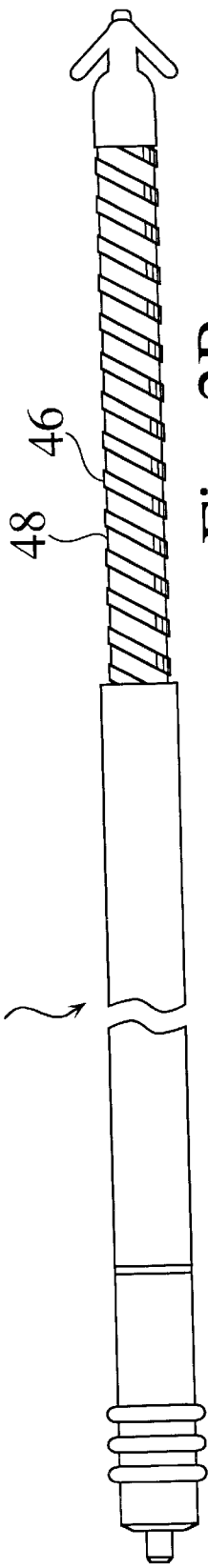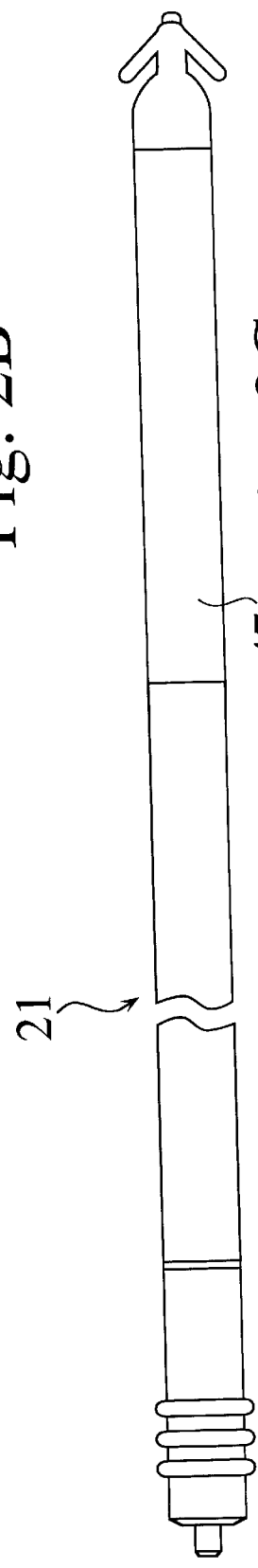

EXPLANTABLE LEAD

FIELD OF THE INVENTION

The present invention relates in general to implantable medical structures, and more particularly to leads and catheters implanted in biological tissues such as the heart. This invention is more specifically directed toward improving the insertion and removal processes of cardiac pacing and defibrillation leads.

BACKGROUND OF THE INVENTION

Various types of transvenous pacing and cardioversion/defibrillation leads have been developed for endocardial introduction into different chambers of a patient's heart, typically the right ventricle (RV) or right atrial (RA) appendage, as well as the coronary sinus (CS). These flexible leads are usually constructed with an outer polymer insulator sheath, such as a flexible silicone or polyurethane tube or coating for encasing one or more coiled or cabled wire electrical conductors. One such conductor is typically attached at its distal tip to the shank portion of a tip electrode. In bipolar or multipolar leads, one or more coiled wire conductors are provided in a coaxial or co-linear relation to a first coiled wire conductor, and are connected to electrodes situated along the lead body. The proximal ends of the conductors are coupled to a connector which includes a single pin in unipolar leads and additional pins or rings in bipolar and multipolar leads.

The tip electrode is usually placed in contact with the myocardial tissue by passage through venous access, often the subclavian or cephalic vein or one of its branches, which leads to the endocardial surface of the heart chambers. The tip electrode may be held in place passively by silicone or polyurethane tines within the trabeculae of the RV apex, as described, for example, in U.S. Pat. No. 3,902,501 to Citron et al. The tines or fins extend outwardly and are usually molded separately and bonded onto the distal end of the lead proximal to the tip electrode. Alternatively, the tip electrode may be held in place actively through the use of a manipulated anchor or screw that penetrates the myocardium, as described, for example, in U.S. Pat. No. 3,974,834 to Kane. These fixation mechanisms help to prevent dislodgment of the tip, thus maintaining consistent sensing and pacing characteristics over time.

Although the state of the art of implantable pulse generators and endocardial lead technology has advanced considerably, endocardial leads nevertheless occasionally fail for a variety of reasons, such as insulation failure, sensing failure, wire conductor fracture, or an increase in electrode resistance beyond a desirable level. Also, in some instances, it may be desirable to add one or more leads to stimulate different portions of the heart than are presently being stimulated with leads already in place. Many patients have one or more, and sometimes as many as four or five previously used (abandoned) and currently used leads in their veins and heart.

The risks of removing leads or introducing additional leads in the heart and venous system include infection, physiological complications, obstruction to blood flow, and formation of blood clots which may embolize to the lung and produce severe complications and even death. In addition, extra leads in the heart can interfere with tricuspid valve and mechanical function, and can cause considerable difficulty in the positioning and attachment of new endocardial leads in the heart.

Typically in the first few months of lead implant, fibrotic tissue encapsulates the lead, especially in areas touching biological tissue, such as the endothelial layer of veins, valves, heart wall, and trabeculae. When small diameter veins through which the lead passes become occluded with fibrotic tissue, separating the lead from the vein becomes difficult and may severely damage the vein or tissue attached to the lead, making lead explant very risky, difficult and oftentimes dangerous.

Several attempts have been made to alleviate the lead explantability problem by using device or tool-assisted methods for removing the lead. A few exemplary lead removal techniques are described in the following publications:

U.S. Pat. No. 4,574,800 to Peers-Trevarton teaches a lead extractor which is inserted into the lumen of an implanted lead and wedged against its inner structure (typically a coil) at a distal location, such as near an electrode implanted in the atrium or ventricle. This wedging condition permits a pulling force to be transmitted along the length of the extractor to the implanted electrode location.

U.S. Pat. No. 5,231,996 to Bardy et al. describes an endocardial lead having a structure that strengthens the lead body to enable its removal by traction after a period of chronic implant. One or more relaxed, nonextensible filaments are loosely contained within the insulating sheath, and have their proximal and distal ends mechanically connected to the connector and electrode shank of the lead. These filaments operate as means for allowing the lead body to reach a stretched length exceeding the relaxed length by an amount sufficient to allow the lead to be stretched without breaking during removal by traction.

U.S. Pat. No. 5,207,683 to Goode et al. teaches the use of a flexible stylet wire with an expandable wire coil attached to the distal end for engaging the coiled structure of the lead.

A potential problem with the above intraluminal devices is that they do not address the possible encapsulating fibrous tissue attached to the lead, either along the lead body or at the distal end, especially with tines. When using these intraluminal extraction devices, the tissue may tear instead of releasing from the lead, causing atrial or ventricular avulsion, tears in the vein or heart, tamponade, and/or hemothorax. Immediate surgical intervention requiring a thoracotomy may be necessary to prevent death.

Other extraction devices have been developed that are meant to fit over the lead to separate the lead from tissue attachments. Such devices are meant to work either alone or in conjunction with intraluminal devices, such as the locking stylets described above. One company that makes such lead extraction tools is Cook Pacemaker Corporation (Leechburg, Pa). However, in many cases, these sheaths are incapable of easily separating calcified tissue from the lead. Often, a femoral removal approach is needed, especially as lead implant duration increases. It is preferred that the leads be removable by the venous implant site rather than femorally, if possible. These extraction sheaths, used alone or in combination with locking stylet devices, do not overcome the risks described above.

In addition to providing special tools to aid in lead extraction, the lead itself may be designed to be more easily extracted, such as by adding coatings, discouraging tissue ingrowth, and making the lead isodiametric. Coated leads and catheters, as well as coating materials are described in the following publications, all of which are incorporated herein by reference:

U.S. Pat. No. 4,487,808 to Lambert describes the process of coating a polymer surface with a hydrophilic coating with low friction under wet conditions. The process comprises applying to the polymer surface a solution containing between 0.05 and 40% of a compound which comprises at least two unreacted isocyanate groups per molecule, evaporating the solvent, applying a solution containing between 0.5 and 50% of polyethylene oxide to the thus treated polymer surface, evaporating the solvent of the latter solution, and curing the coating at elevated temperature. This patent aims at facilitating the insertion of medical instruments inside a body cavity by decreasing the coefficient of friction of the surface of the device or lead.

U.S. Pat. No. 5,041,100 to Rowland et al. describes a catheter to which a friction-reducing coating may be applied, to reduce catheter friction particularly when the coating is hydrated. The coating includes a mixture of a structural plastic material and high molecular weight polyethylene oxide, for facilitating the insertion of the catheter into a patient's body.

U.S. Pat. No. 5,077,352 to Elton describes still other abrasion resistant, hydrophilic, lubricious organic coatings for application to the outer surfaces of inorganic materials or organic polymeric medical devices, to facilitate the introduction of these devices inside the patient's body.

However, while the foregoing coating processes may reduce friction to aid in implanting the leads, none of them were developed for nor adequately addresses the problem of explantation of leads should adhesions develop on the surface and become firmly attached. It appears that in prior art only a thin, surface coating is applied, with no significant dimensional changes. Only a thin coating is necessary to reduce friction to facilitate ease of insertion.

Hydrogel coatings have been proposed for other uses in pacing and defibrillation leads. The following are such examples, and are incorporated herein by reference:

European patent application No. 057,450 to Cahalan et al. relates to a body implantable lead having a polymer-based gel electrode. European patent application No. 057,451 to Juncker et al. relates to a body implantable lead having a pressure-cushioned electrode. In both cases, the pacing tip electrode is coated with a hydrogel, thus separating the solid electrode from the excitable tissue and increasing the effective electrode area. While increasing effective electrode area is desirable for defibrillation in which the goal is field stimulation, it is desirable to keep effective pacing electrode area small to minimize pacing thresholds. Therefore, increased pacing thresholds would be a disadvantage for the Cahalan et al. and Juncker et al. inventions.

1995 NASPE abstract 452, entitled "A New Surgical Temporary Pacing Lead: Easy to be Fixed and Easy to be Removed," by Yokoyama et al. describes the use of a material composed of absorbable polyglycolic acid felt (PGA felt) for facilitating the extraction of temporary pacing leads seven to ten days after implantation. However, there is no clear indication that this material can be useful to resolve fibrotic encapsulation problems resulting from the long term implantation of the lead, since the PGA felt is absorbed by the tissue after ten days, and tissue encapsulation may then begin. Additionally, the use of the PGA felt seems to be limited to the distal end of the lead, and consequently neglects the fibrotic growth on the defibrillation electrode and lead body.

U.S. Pat. No. 5,020,544 to Dahl et al. describes a defibrillation patch electrode having a hydrogel incorporated in the porous conductive screen for preventing tissue ingrowth. The hydrogel can serve as a drug reservoir for antibiotics, antiseptics, antiarrhythmics, or anti-inflammatory steroids.

Polymer hydrogels and other coatings have also been recommended for use on implantable devices to stimulate the attachment of endothelial cells for improving thrombo-resistance. U.S. Pat. No. 4,836,884 to McAuslan describes such hydrogels.

U.S. Pat. No. 5,090,422 to Dahl et al. describes a porous implantable enclosure that covers and isolates an electrode in a way which allows electrical coductivity via bodily fluid which passes through but separates the electrode from the adjacent tissue in the manner of a dissection plane which substantially prevents tissue ingrowth. In addition to the improved explantability, the porous covering is also intended to reduce tissue burning and edema. However, the porous implantable enclosures in Dahl are not described as expandable, so that the lead would have to be implanted with the covering already at the final thickness required to provide the desired effects, which is disclosed as 10 to 100 mils. This would increase the overall diameter of the lead by 20 to 200 mils (up to about 5 mm), which would substantially increase the introducer size needed and reduce maneuverability through the vein to the implant sight.

While the foregoing coating processes may aid in preventing tissue ingrowth into the interior of the leads, none of them adequately addresses the problem of explantation of leads should adhesions develop on the surface and become firmly attached. It appears that only a thin, surface coating is applied, with no significant dimensional changes.

None of the above solutions completely satisfies the need for a new method and lead structure which is easy to implant and improves the rate of successful lead explantation, particularly after the encapsulated tissue has rendered various traction removal methods impractical.

SUMMARY OF THE INVENTION

The present invention is directed toward optimizing the construction of implantable leads and catheters for chronic blood contacting use. In particular, the present invention is directed toward improving the extractability of a permanently implanted cardiac lead.

It is a further object of the present invention to provide a new lead that can be withdrawn from any encapsulating tissue that may form with relatively little or no damage to either the lead or the neighboring body tissue.

Briefly, the foregoing and other objects of the present invention are realized by a new hydrogel-coated lead as described below. In the coatings of the present invention, preferably, hydrogels having a thickness increase greater than 10% are used. A thicker coating is used to provide a shear layer so that the coating tears during extraction, either at the coating/lead interface, between layers of the coating itself, or at the coating/tissue interface. Furthermore, because of the flexibility of such a thick coating, contracture of any fibrous capsule that may have formed is not a problem during extraction, since instead of contracting onto the lead body itself, it contracts onto the flexible, slippery coating which can be extracted out of the tight capsule.

BRIEF DESCRIPTION OF THE DRAWINGS

The various features and advantages of the present invention may be more readily understood with reference to the following detailed description taken in conjunction with the accompanying drawings in which:

FIGS. 2A, 2B, and 2C are side views of three embodiments of the RV lead of FIG. 1;

Similar numerals refer to similar elements in the drawings. It should be understood that the sizes of the different components in the figures may not be to scale or in exact proportion, and are shown for visual clarity and for the purpose of explanation.

DETAILED DESCRIPTION OF THE INVENTION

Figure 1:
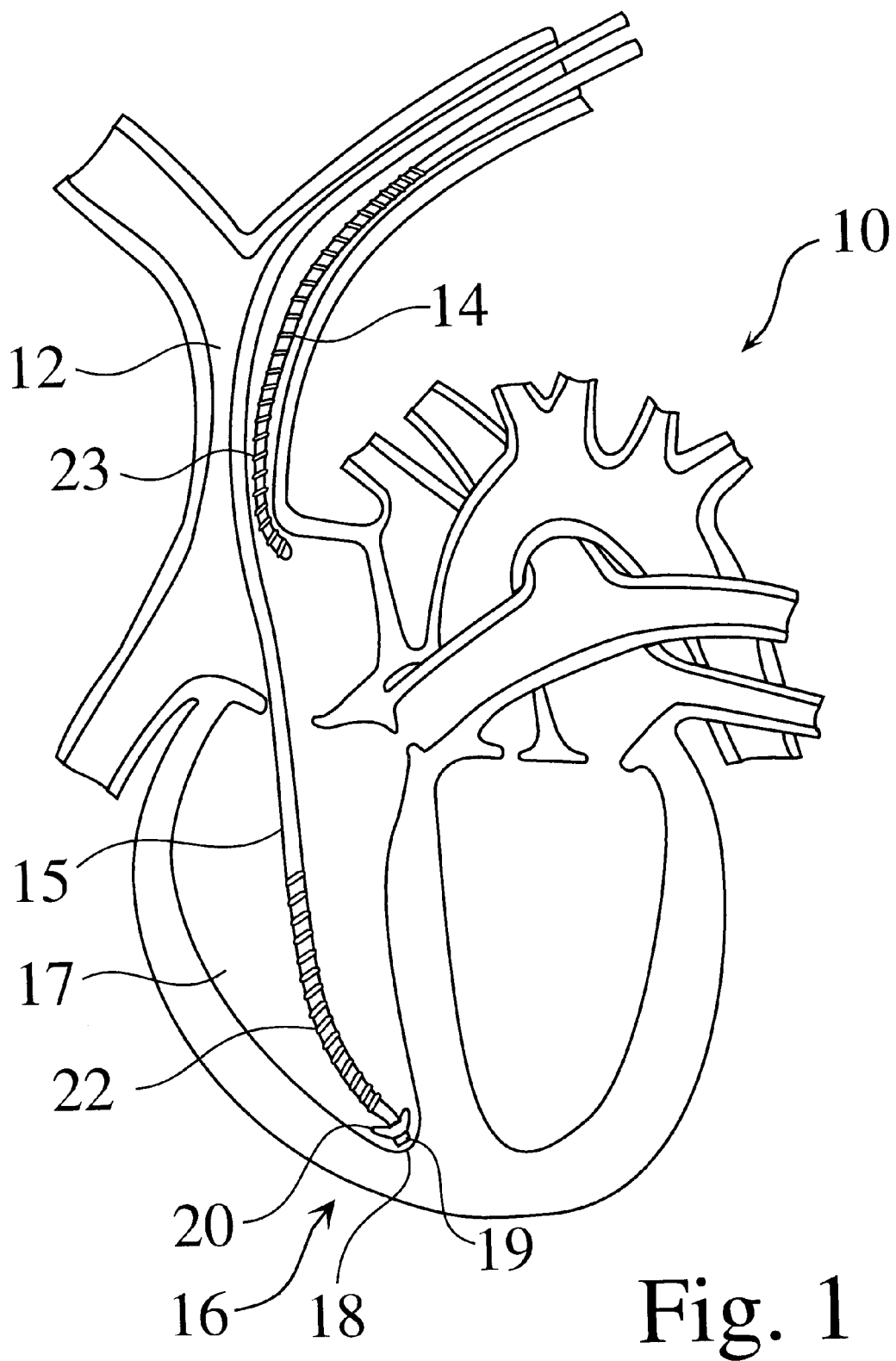
FIG. 1 is a side view of a transvenous SVC lead and an RV lead made according to the present invention, and shown implanted in a heart.

FIG. 1 illustrates a heart 10 and a superior vena cava (SVC) 12 through which an SVC lead 14 and a right ventricular (RV) defibrillation lead 15 are implanted. The RV lead 15 passes through the SVC 12 into the RV 17 of the heart 10. The distal end 16 of the RV lead 15 includes a pacing tip electrode 19 for electrically stimulating the heart 10. The distal end 16 is secured to trabeculae within the apex 18 of RV 17 by means of a plurality of tines 20, which in time become securely attached by fibrotic tissue forming around tines 20. RV lead 15 further includes a defibrillation electrode 22 which may rest against the heart wall and may mechanically stimulate the growth of fibrotic tissue around it. Defibrillation electrode 22 may also serve as a sensing electrode and/or as the return electrode for bipolar pacing. Alternatively or additionally, lead 15 may include one or more electrodes dedicated for sensing and/or pacing return electrodes (not shown).

The SVC lead 12 includes an electrode 23 which also may become secured to the vein wall through fibrotic growth and encapsulation. A lead for implantation in the CS may also be constructed similarly to SVC lead 14, and be preferably 6 French or less in diameter during insertion, prior to hydration. A lead having good extractability may be even more important for the CS than for other locations because of proximity to tissue, smaller space possibly more prone to occlusion, weakness of venous tissue as compared to myocardium, a more tortuous path, and more complex lead configuration. For an example of a complex CS lead configuration, see U.S. Pat. No. 5,476,498 to Ayers which is incorporated herein by reference.

FIGS. 2A, 2B, and 2C provide overall views of three embodiments of RV lead 15, which include a lead body 21, that is attached to a connector 25 and insulated by insulation 24. As it will be described later in greater detail, selected parts of RV lead 15 are coated with a thin hydrophilic polymer layer. The hydrogel layer forms a coating 30 over tines 20, a coating 32 over defibrillation electrode 22, and a coating 34 over lead insulation 24.

It is not necessary to apply the hydrogel to the connectors, the pacing tip electrode, or the region of the lead that will be coiled into the subcutaneous area. If the pacing tip electrode were coated, tissue would not grow into the pores, thereby not providing firm stabilization of the lead at the tip. This in turn would lead to mechanical rubbing between the tip and the cardiac tissue, leading to increased scar tissue formation. This increase in nonstimulatable tissue layer thickness, coupled with the thickness of the coating itself, would mean that the virtual electrode area for pacing would be increased to an undesirable level and require more energy.

In FIG. 2A, the conductive electrode material of defibrillation electrode 22 is made up of small diameter coils 45 wrapped around lead body 21. Details of this type of construction are given in U.S. Pat. No. 5,439,485 to Mar et al. which is assigned to the assignee of the present invention and is incorporated herein by reference. In FIG. 2B, the conductive electrode material is made up of wire 46 wrapped around and secured to lead body 21. In FIG. 2C, the conductive electrode material is a conductive polymer 47.

Figure 3:
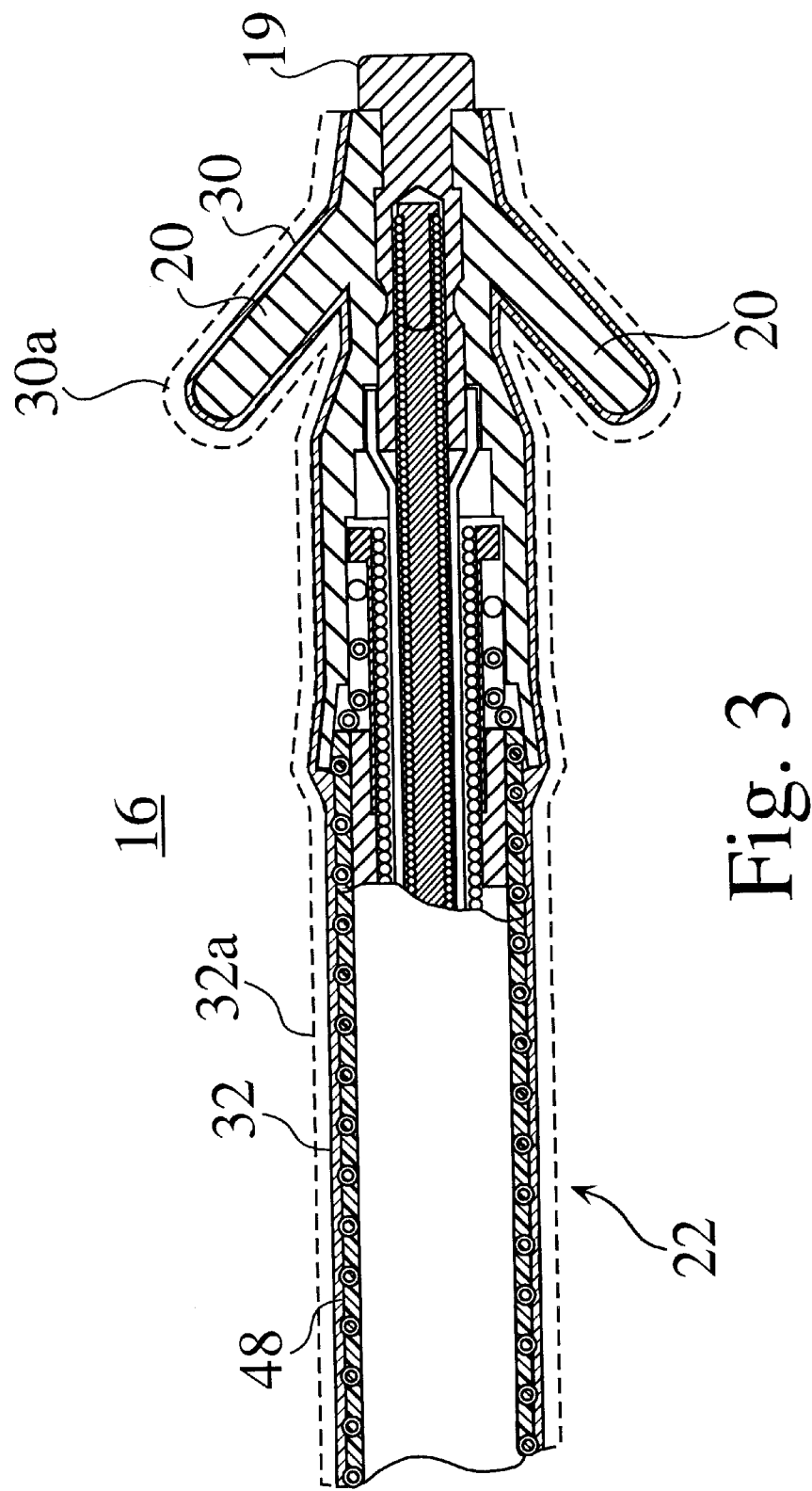
FIG. 3 is a greatly enlarged cross-sectional view of the distal end of the RV lead of FIG. 2A.

FIG. 3 illustrates a more detailed view of the distal end 16, and illustrates the coating 30 prior to implantation (in solid line) and after implantation (in dashed lines). Before implant, the hydrogel layer is a thin coating on the surface of lead 15. At implant, the hydrogel layer absorbs body fluids and expands in volume. This feature is illustrated by way of example, by the expanded coating 30a shown in dashed lines around tines 20. As the dry coating 30 becomes hydrated, its structure changes: its volume increases, and it becomes softer and mechanically weak, but not so weak as to be susceptible to ordinary biological and mechanical degradation mechanisms to which leads are typically subjected. As a result, the hydrogel layer acts as a mechanical buffer between lead 15 and the encapsulating fibrotic tissue, and prevents the encapsulating fibrotic tissue from attaching directly onto the polymeric surface, e.g., silicone, of tines 20, defibrillation electrode 22, and lead insulation 24. Furthermore, in the event that encapsulating fibrotic tissue forms on the hydrogel, because the hydrogel is compliant and has a low coefficient of friction, the lead can be pulled out more easily.

Because the hydrogel prevents fibrotic tissue from attaching directly to the polymeric or metallic surfaces of the lead, and because the hydrated hydrogel layer is weak, in the event that lead explantation is required, the hydrogel layer can act as a shear layer. Consequently, lead 15 may be easily removed from the encapsulating fibrotic sheath with minimal or no damage to neighboring body tissue. While it would be preferable to remove the entire hydrogel layer during explantation, part of the hydrogel layer may be left in the heart. The residual layer will not cause damage to the heart, since it is biocompatible, being composed mostly of water with similar ionic content to that of blood. The residual layer will occupy a small volume and is mechanically compliant and soft to prevent mechanical irritation.

As used herein "hydrogel" or "hydrogel layers" includes a polymer that expands in volume when it hydrates. The following are some exemplary hydrogels: Poly 1-hydroxyethyl methacrylate, polymethacrylic acid, poly(N, N, dimethyl-aminoethyl methacrylate), polyacrylamide, poly(N-vinyl pyrrolidone), polyvinyl alcohol, polyethylene oxides, hydrolyzed polyacrylonitrile, polyelectrolyte complexes, polymethacrylic acid and polyacrylonitrile, anionic and cationic hydrogels or composites or copolymers of one or more of these hydrogels and other suitable biocompatible materials such as silicone, polymers, and polyurethane.

In one embodiment the hydrogel can be used as a vehicle for drug delivery, by loading the polymeric hydrogel precursor with a blood soluble or insoluble drug, or by chemically binding a drug such as antibiotic, antiseptic, antiarrhythmic, antiinflammatory steroid or other agents, to the polymer network. Upon expansion of the hydrogel layer, the drug is released to the neighboring tissue.

The hydrogel can also be loaded with an additive, such as $Na^+Cl^-$ or other electrolyte, to enhance its electrical conductivity. It is preferred that the hydrated coating consist mostly of water with an ionic content at least that of blood. Examples of loading methods include dissolving a salt in a monomer-water-initiator solution and polymerizing, or simply soaking the unloaded, coated lead in an electrolyte solution.

The hydrogel may also be blended with a non-hydrogel polymer that increases the physical strength and/or helps control the degree of swell, while the hydrogel carries the electric current. Methods for preparing hydrogel/non-hydrogel polymer blends are known in the art, with an example being described in U.S. Pat. No. 4,883,699 to Aniuk et al., which is incorporated herein by reference. A mixture of the components can be prepared using, for example, a two-roll mill, an internal mixer, such as a Brabender or Banbury mixer, and extruder, for example a twin-screw extruder.

Depending on the thickness of the hydrogel, the expanded hydrogel layer may reduce stimulation edge effects. It may further allow a more uniform distribution of the stimulation energy for decreasing the chance of tissue damage. The biocompatibility and dimensional and chemical stability of hydrogels render them well-suited for long-term implantation. The expanded hydrogel layer may also inhibit tissue adhesion and thrombus formation on the lead.

In one embodiment, the hydrogel layer is formed on lead 15 by dip coating predetermined parts of lead 15 in a hydrogel solution. Other exemplary coating techniques include molding, spraying, and vapor deposition. Alternatively, a fully crosslinked hydrogel tube may be hydrated, inserted over a lead, and allowed to dry onto the lead. Primer and/or adhesive may be added at the interface that is activated by heat or UV.

In some applications, it is desirable to enhance the adhesion of the hydrogel layer to either the lead body or the electrodes. Several methods may be used to accomplish such result, such as ion etching, covalent crosslinking, thermal or chemical surface treatment, radiation (i.e., electron or gamma beam), and adding a primer layer between the lead and the hydrogel layer.

Figure 4:
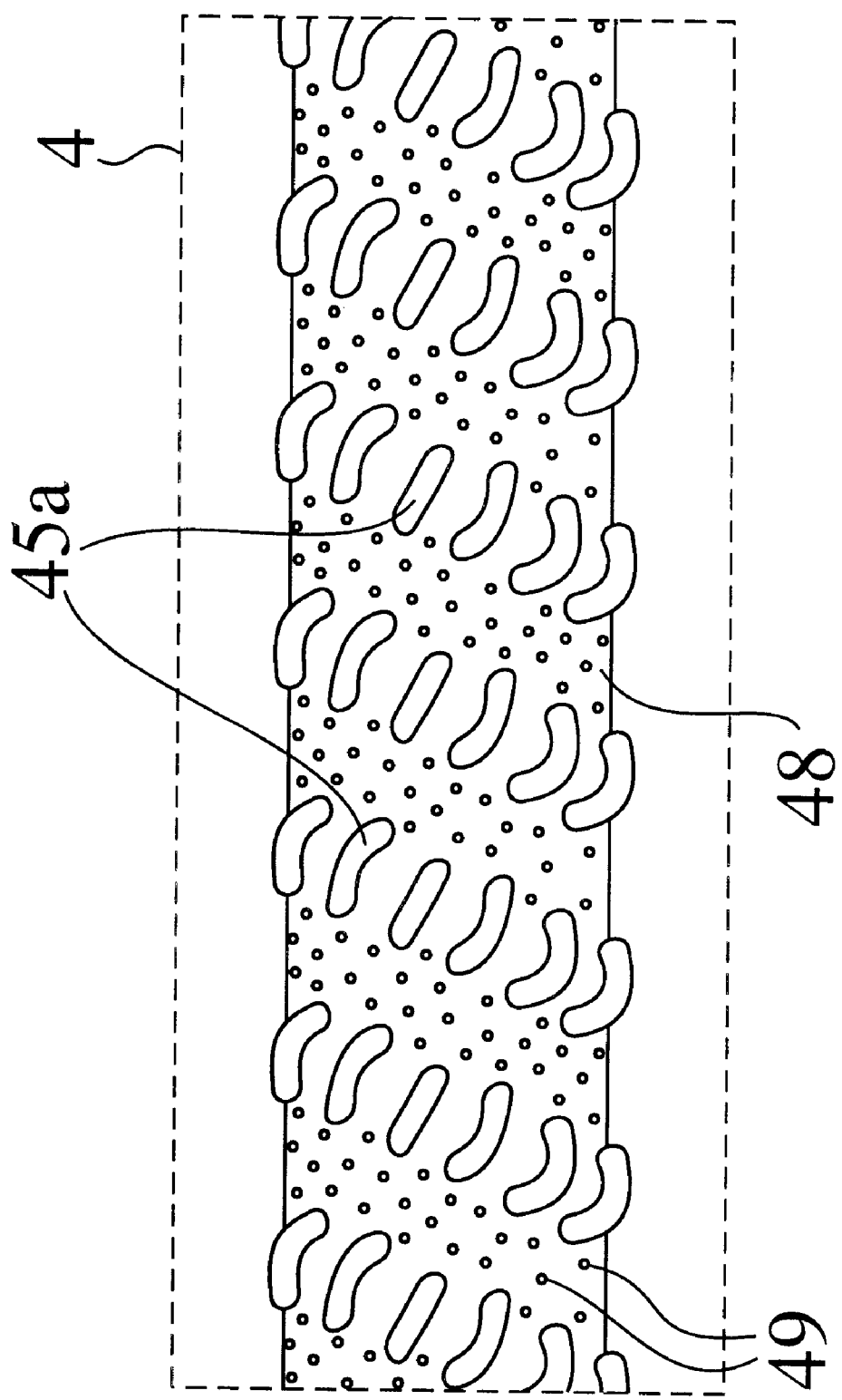
FIG. 4 is a greatly enlarged view of part of a defibrillation electrode forming part of the RV lead of FIG. 2A and shown inside a square loop 4 of FIG. 2A.

Defibrillation electrode 22 and coating 32 may be formed as illustrated in FIG. 4, which is a greatly enlarged surface view of FIG. 2A. It includes wrapping conductive coiled wires 45 around lead body 21, and then coating RV electrode 22 with an insulation layer 48, such as a urethane or silicone layer. Insulation layer 48 defines raised portions over the conductive coils 45, which raised portions are then ablated for allowing portions 45a of the coiled coils 45 to be exposed. In one embodiment, the outer surface of insulation layer 48 is treated, such as by applying a primer, to produce active sites 49 for binding to the hydrogel. A hydrogel layer is then formed or deposited over insulation layer 48. Additionally, if hydrogel is desired onto the metal portions, the metal may be etched and or primed to improve adhesion of hydrogel.

Figure 5:
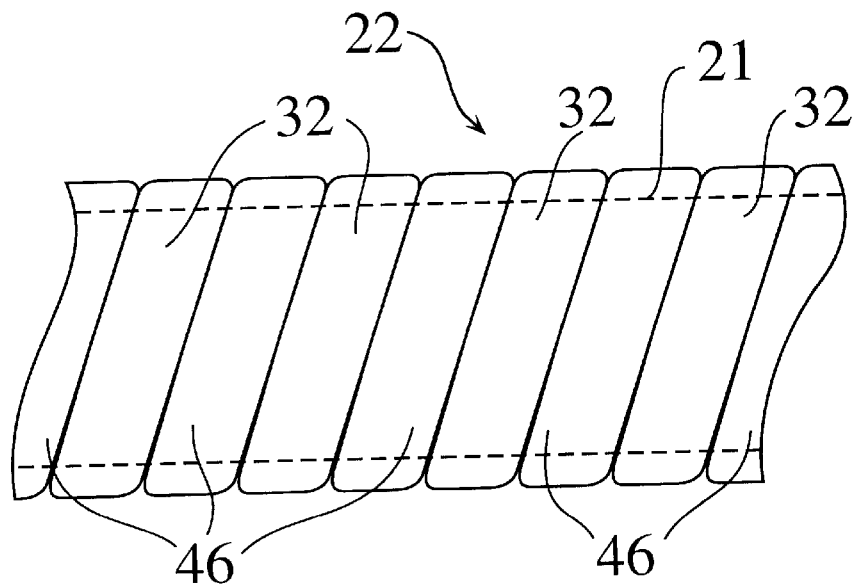
FIGS. 5 and 6 represent enlarged side elevational views of part of a defibrillation electrode of the RV lead of FIG. 2B, showing a hydrogel coating deposited between the conductive coils of the defibrillation electrode.
Figure 6:
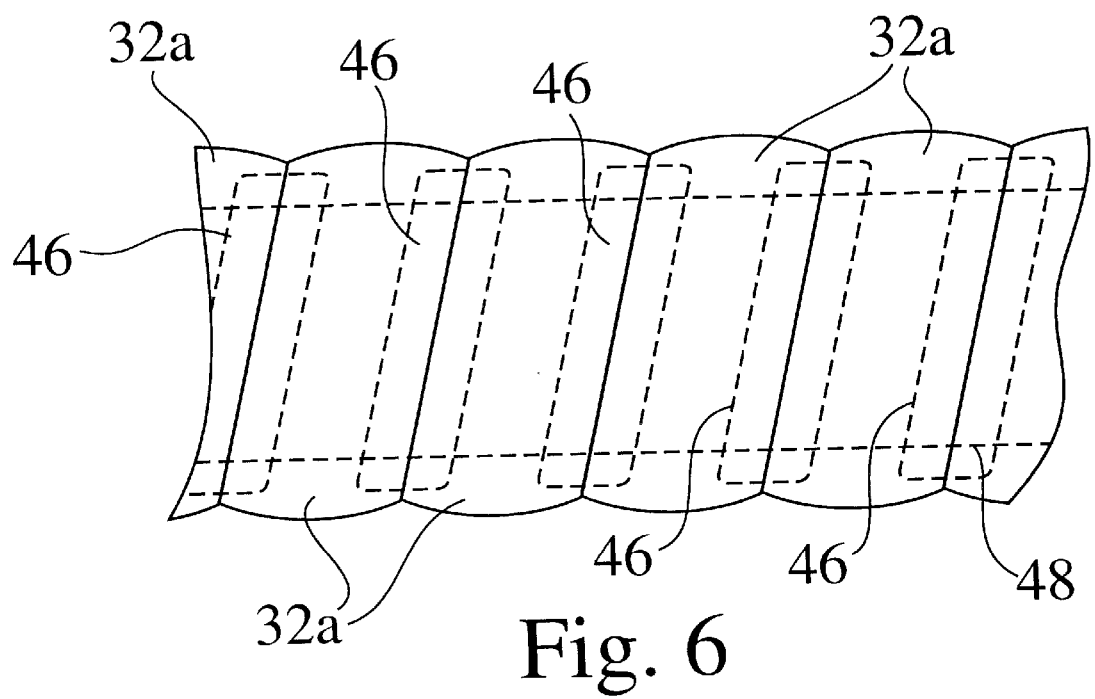

FIGS. 5 and 6 illustrate another way to form the coating of the defibrillation electrodes, for instance RV electrode 22 of FIG. 2B. RV electrode 22 is formed of one or more conductive wires 46 wound around lead body 21 (shown in dashed lines). A thin dry hydrogel coating 32 is formed on the portions of lead body 21 that are not covered by wire 46. Coating 32 may be formed by dipping RV electrode 22 in a hydrogel solution, and by allowing the hydrogel layer to dry. Coating 32 preferentially adheres to the material of lead body 21, which is typically silicone, and does not adhere as well to the wire 46, which is typically platinum or a platinum iridium alloy. Lead 15 may be dipped beyond electrode 22 such that portions of lead insulation 24 (not shown) are also coated. FIG. 6 illustrates the swelling of coating 32 after implantation and hydration, to form a pliant coating 32a, that covers the conductive wire 46 (shown in dashed lines). Expanded coating 32a may cover the wire 46 entirely or partially, depending on the volume swell of hydrogel coating 32.

Figure 7:
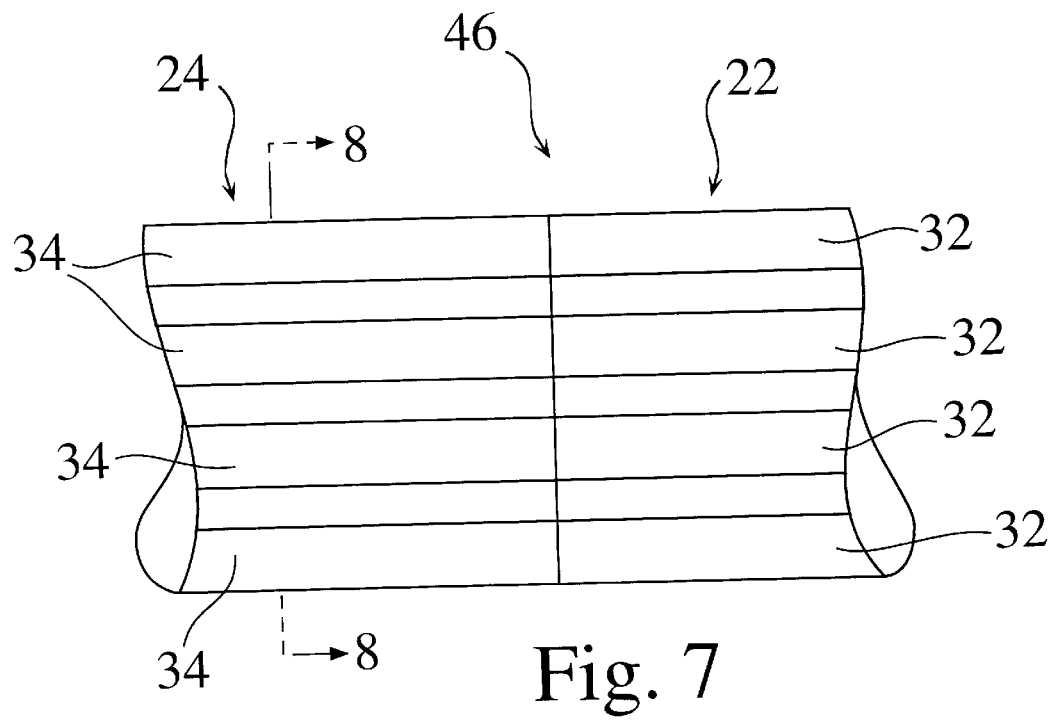
FIG. 7 is an enlarged side view of an alternative defibrillation electrode with longitudinal strips of a hydrogel coating.

FIG. 7 is an enlarged side view of an alternative lead body 21 showing coatings 34 and 32 of insulation 24 and defibrillation electrode 22 in the form of longitudinal strips of a hydrogel coating. The strips may be rectangular, semicircular, or other shapes in cross section.

Figure 8:
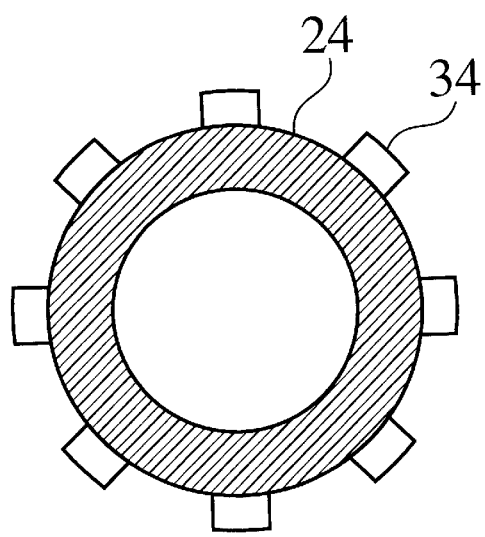
FIG. 8 is a cross-sectional view of the defibrillation electrode of FIG. 7, taken along line 8—8.

FIG. 8 is a cross-sectional view of the defibrillation electrode of FIG. 7, taken along line 8—8. (The inner coil structure has been omitted from the drawing for clarity.)

Figure 9:
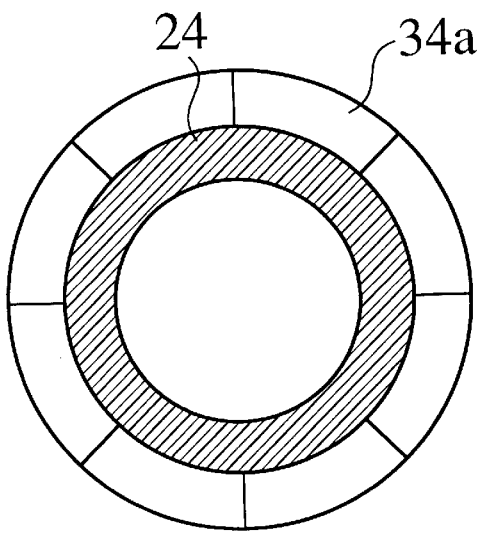
FIG. 9 is a cross-sectional view of the defibrillation electrode of FIG. 8, illustrating an expanded hydrated layer.

FIG. 9 is a cross-sectional view of the defibrillation electrode of FIG. 8, illustrating an expanded hydrated hydrogel layer 34a.

Figure 10:
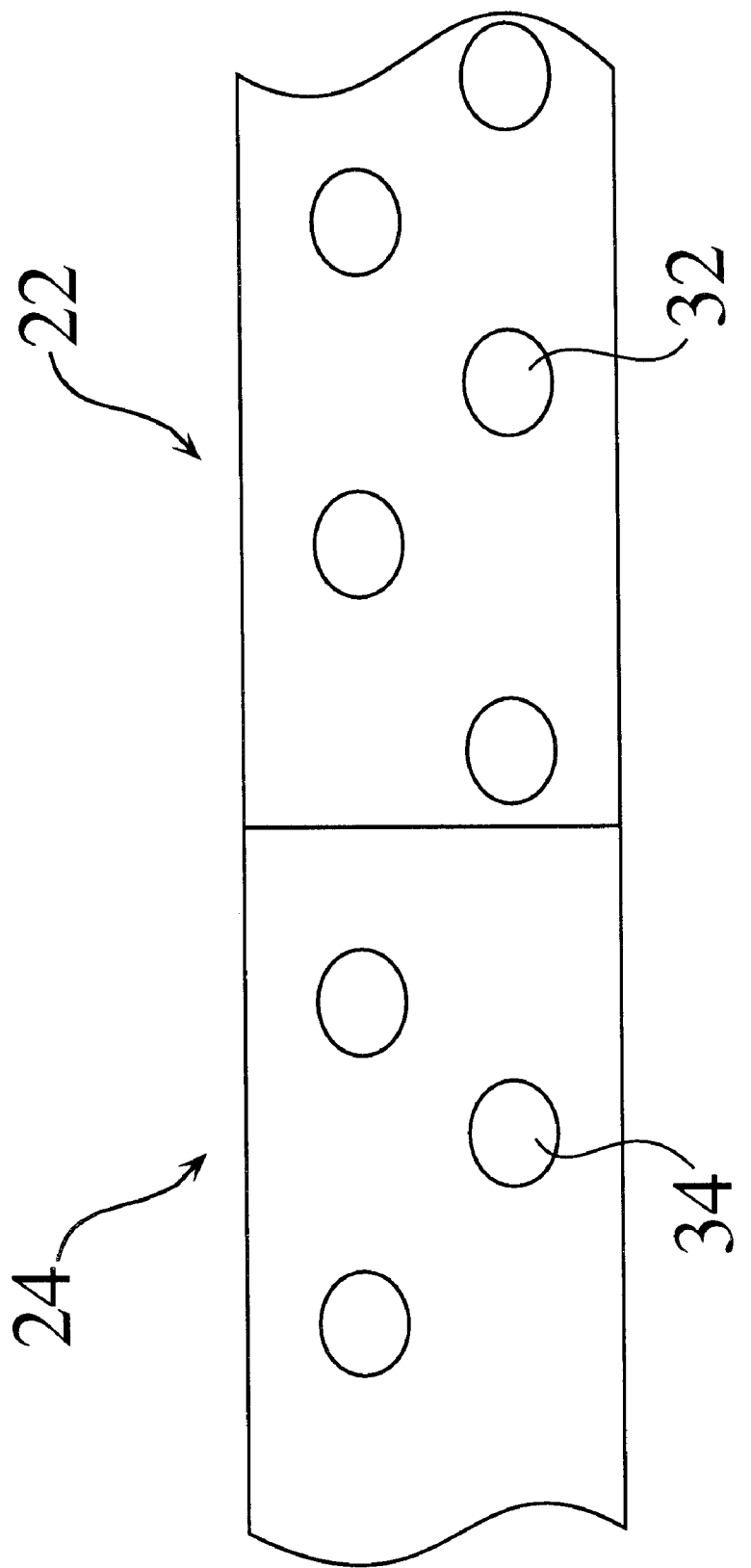
FIG. 10 is an enlarged side view of an alternative defibrillation electrode with a dot pattern of hydrogel applied.

FIG. 10 is an enlarged side view of an alternative arrangement of hydrogel coatings 34 and 32 of insulation 24 and defibrillation electrode 22, respectively, with a dot pattern of hydrogel applied. The hydrogel may be applied in any pattern.

Figure 11:
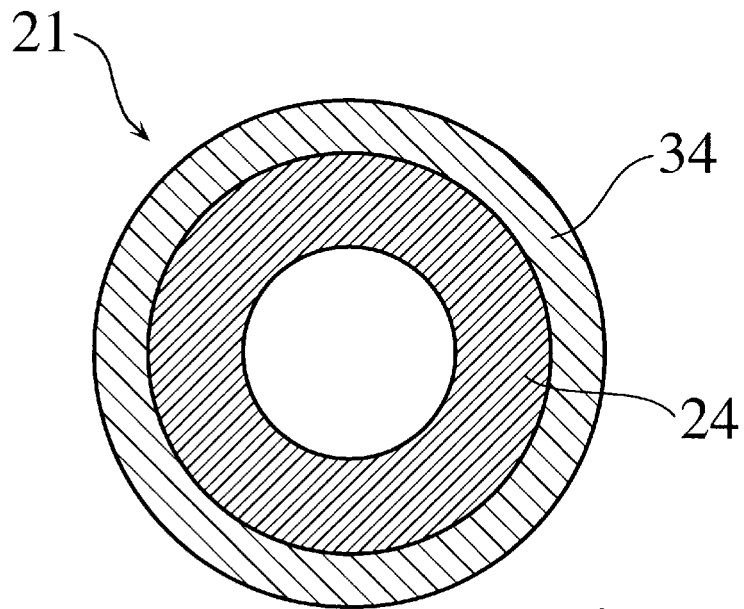
FIGS. 11 and 12 are enlarged cross-sectional views of the outer sheath of the lead body shown in FIG. 2A, taken along line 11—11, shown prior and subsequent to implant.
Figure 12:
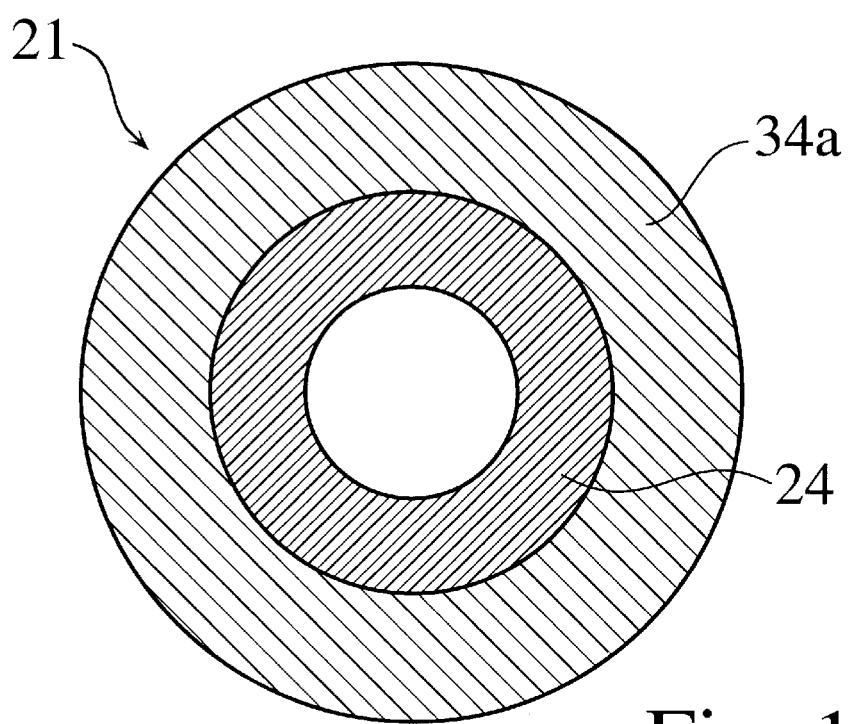

FIGS. 11 and 12 are cross-sectional views of lead body 21, taken along line 11—11 in FIG. 2A. Lead body 21 includes a biocompatible, insulative outer sheath 24 which is coated with a thin dry hydrogel layer 34. FIG. 12 illustrates the expansion of hydrogel layer 34 into a swollen pliant coating 34a after implant and hydration. As explained above, coating 34a provides a shear layer between outer sheath 24 and attached fibrous encapsulation, and therefore facilitates the explantation of lead 15. In one embodiment of lead 15, hydrogel layer 34 is not applied to the entire length of outer sheath 24, but rather on selected portions of outer sheath 24 that are more likely to be encapsulated by fibrous tissue.

Preferably, the dry, unexpanded hydrogel coating thickness is 0.1 to 0.5 mm, and the hydrated, expanded thickness is approximately 0.25 to 1.5 mm, and most preferably about 0.5 to 1 mm. Therefore, a typical dry, coated lead may start out with a diameter of about 3 mm; when the coating is expanded, the final lead diameter may be about 4 mm. When the dry lead becomes hydrated, the increase in the hydrogel layer thickness itself is preferably greater than 10% and less than 500%.

It is preferred that hydration take place quickly enough to perform standard implant testing without delay following lead insertion. Therefore, hydration can occur any time between the time the lead leaves the end of the introducer and about one minute following positioning, preferably about 30 seconds.

With these properties, while maintaining small size for ease of implant through an introducer, the electrode is effectively enlarged and explantability is improved. The enlargeability of the electrode diameter leads to reduced peak current density and more even current distribution, which may serve to decrease incidence and severity of burns, edema, necrosis, and or tissue stunning. Furthermore, if high current density areas are refibrillatory, by reducing them, defibrillation thresholds may actually be lowered, thereby allowing lower energies to be used and prolonging battery life.

Figure 13:
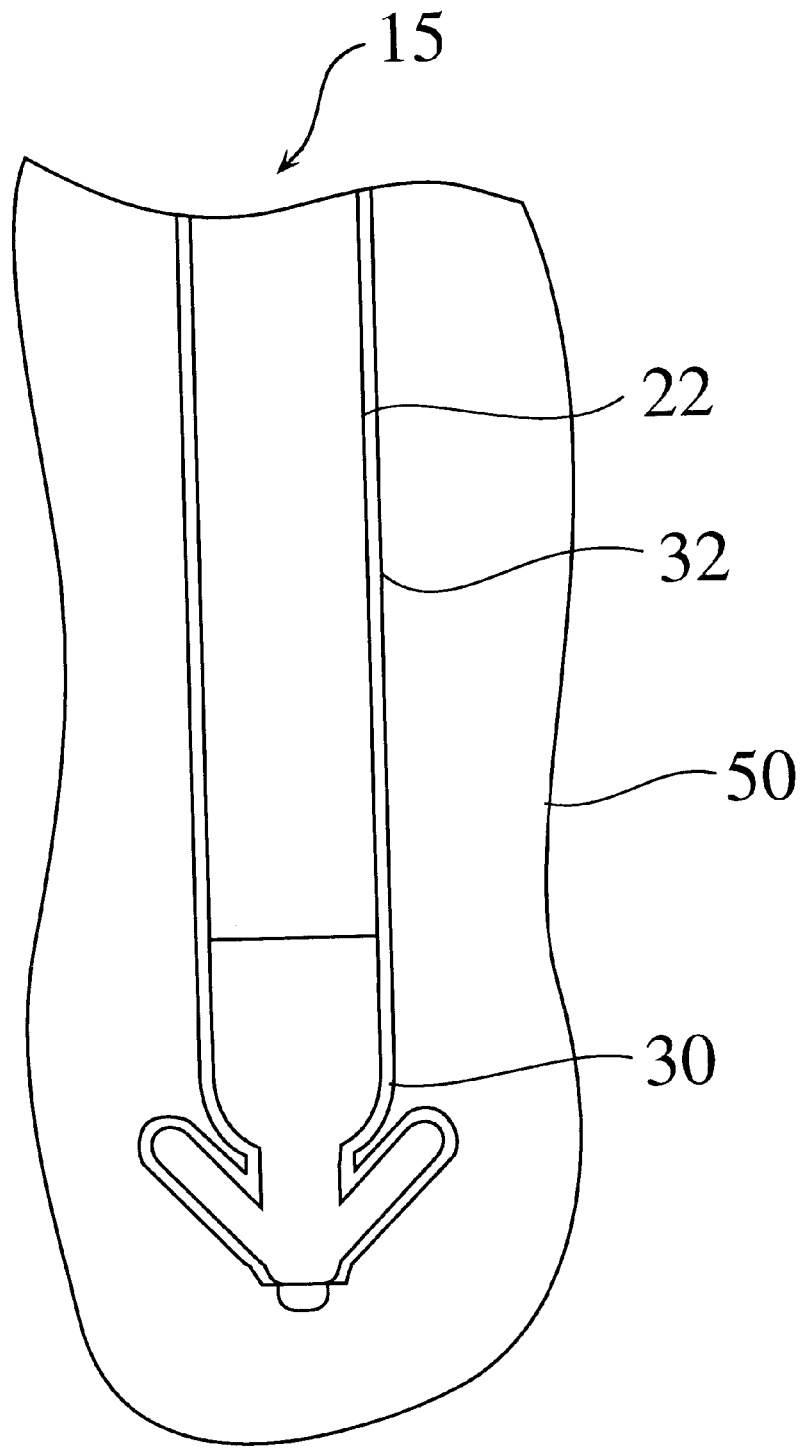
FIG. 13 is a side view of the RV lead of FIG. 1 shown encapsulated in a tissue sheath.

FIG. 13 is a side view of lead 15 of FIG. 1 shown encapsulated in a tissue sheath 50. FIGS. 14A, 14B, 15A, 15B, 16A, and 16B are side views of the RV lead of FIG. 1 being explanted from the heart. Because the tissue response will occur at the outer surface of hydrogel 32, the tissue capsule 50 would be separated from electrode 22 by the hydrogel layer. This facilitates easy removal of the electrode from the tissue sheath. The hydrogel is mechanically very weak and acts as a shear layer to allow the electrode to easily pull away from the tissue sheath. The ultimate tensile strength (UTS) of fibrous capsule has been reported at 334 psi, and the UTS of typical silicone rubber, a major component of leads, is 900 psi. Cardiac muscle has a UTS of 16 psi, and veins have a UTS of 247 psi in the longitudinal direction. Thus, a hydrogel with an ultimate tensile strength of 1 to 300 psi would provide a weak link for allowing the lead to break free from the fibrous tissue.

Lead 15 is extracted from the tissue capsule 50 by applying traction at a proximal portion of the lead, such as the connector end 25 (shown in FIG. 2A) or at an accessible portion of the lead body 21 where it exits the venous access site (not shown). A twisting motion may be used to aid in separating the lead from the tissue capsule. A locking stylet-type device and/or an extraction sheath (as described herein under Background) may be used to aid in this separation process.

Figure 14A:
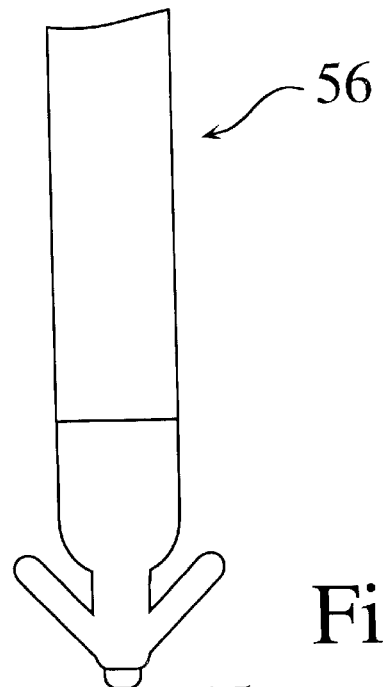
FIGS. 14A, 14B, 15A, 15B, 16A, and 16B are side views of the RV lead of FIG. 1 being explanted from the heart.
Figure 14B:
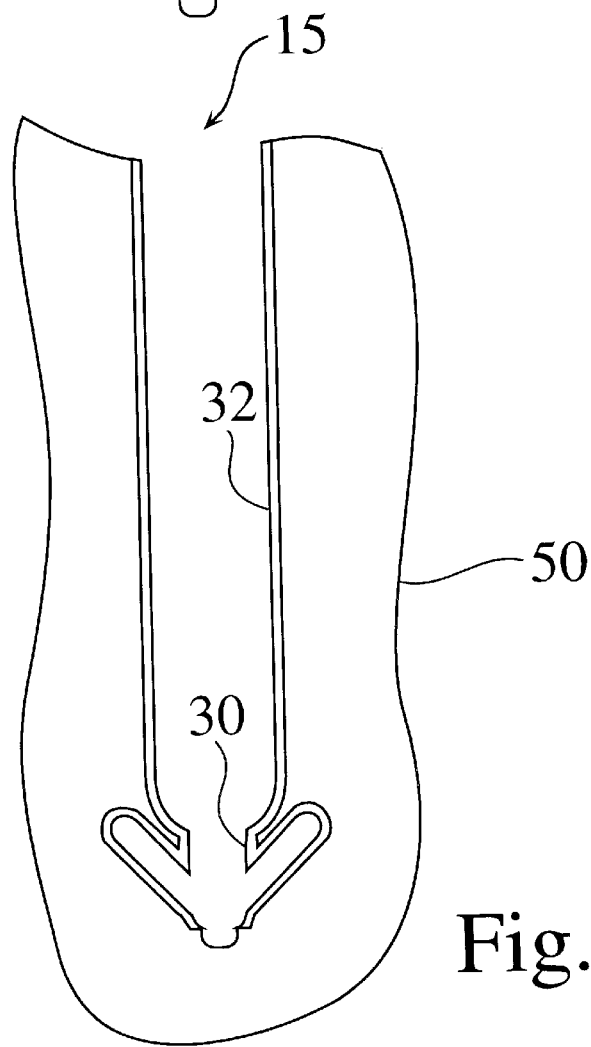
Figure 15A:
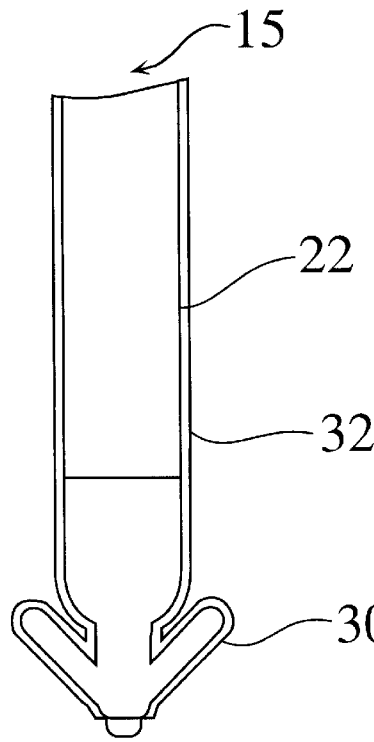
Figure 15B:
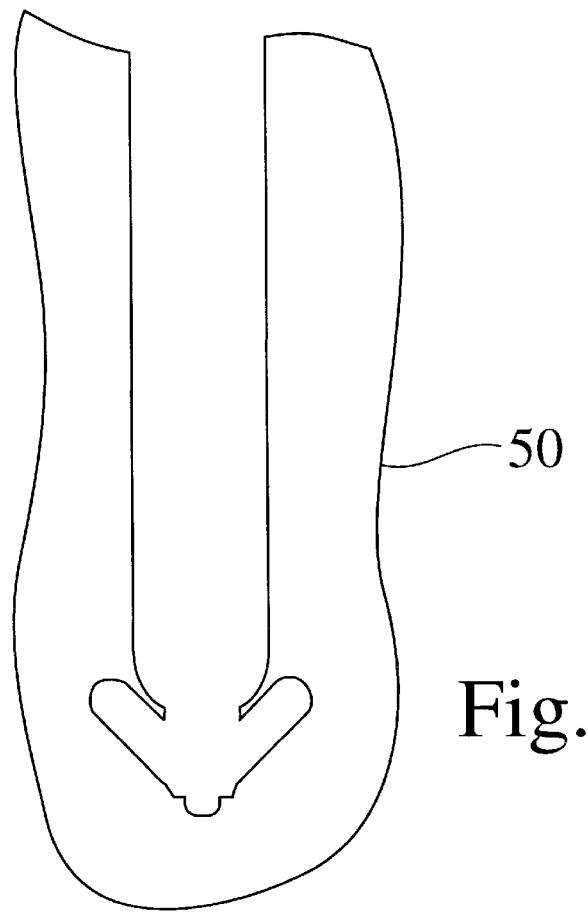
Figure 16A:
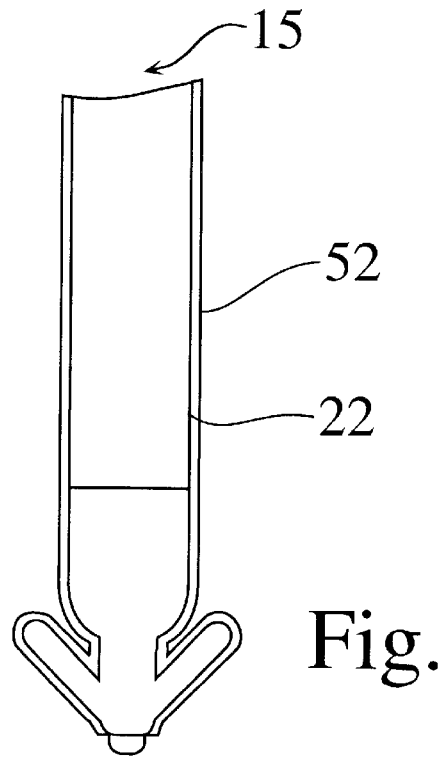
Figure 16B:
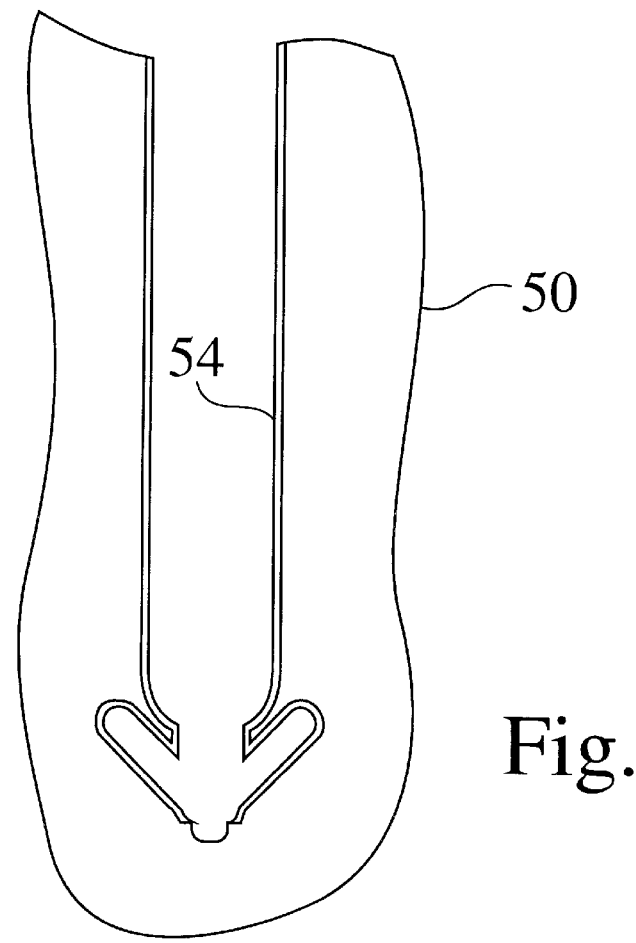

In FIGS. 14A and 14B, lead 15 is shown separated from tissue 50 between hydrogel coating 30, 32 and the rest of the lead 56 (lead 15 minus the hydrogel coating). In FIGS. 15A and 15B, lead 15 is shown separated from tissue 50 between hydrogel coating 30, 32 and tissue 50. In FIGS. 16A and 16B, lead 15 is shown separated from tissue 50 by separating hydrogel coating 30, 32 into layers, leaving the extracted lead with a first layer 52 of coating and leaving a second layer 54 of hydrogel coating attached to tissue 50. The extraction process may involve a combination of separations, with portions of the encapsulated lead separating between the coating and the rest of the lead, other portions separating between layers of the coating, and still other portions separating between the coating and the tissue. Alternatively, the extraction process may be primarily limited to only one type of separation, with only a small amount of hydrogel coating remaining adherent in patches to either the rest of the lead or to the tissue.

While the foregoing embodiments were explained in relation to RV lead 15, it should be understood that the same or similar inventive concepts may be applied to SVC (or CS) lead 14 as well as to other implantable medical structures in the venous system, including other defibrillation leads, catheters, and pacemaker leads.

It should be understood that various alternatives to the embodiments of the invention described herein may be employed in practicing the invention. It is intended that the following claims define the scope of the invention and that structures and methods within the scope of these claims and their equivalents be covered thereby.

What is claimed is:

1. An implantable cardiac lead comprising:
   a lead body portion having an outer surface, a distal end, and a proximal end, for transvenous implantation in the body of a patient;
   a hydrogel layer at least partially covering said outer surface of said lead body, wherein said hydrogel layer is between about 0.25 mm and 1.5 mm thick when hydrated with bodily fluids.

2. The lead of claim 1 wherein said hydrogel layer has a hydrated ultimate tensile strength of between about 10 and 300 psi.

3. The lead of claim 1 wherein said hydrogel is chosen from a group consisting of: poly (2-hydroxyethyl methacrylate); poly(methacrylic acid); poly(N,N, dimethylaminoethyl methacrylate); polyacrylamide; poly (N-vinyl pyrrolidone); polyvinyl alcohol; polyethylene oxide; hydrolyzed polyacrylonitrile; polyelectrolyte complex; polyacrylonitrile; anionic hydrogel; cationic hydrogel; composite of one or more of the preceding hydrogels and silicone; composite of one or more of the preceding hydrogels and polyurethane; copolymer of one or more of the preceding hydrogels and silicone; and copolymer of one or more of the preceding hydrogels and polyurethane.

4. The lead of claim 1 wherein said hydrogel layer has a thickness increase of greater than 10% when hydrated.

5. The lead of claim 4 wherein said hydrogel layer has a thickness increase of less than 500% when hydrated.

6. The lead of claim 1 wherein said lead body portion includes tines located at a distal end of said lead body portion and wherein said hydrogel layer is located on said tines.

7. The lead of claim 1 wherein said lead body portion further comprises a defibrillation electrode portion located proximal of said distal end and wherein said hydrogel layer at least partially covers said defibrillation electrode portion.

8. The lead of claim 7 wherein said defibrillation electrode is adapted for placement in the coronary sinus.

9. The lead of claim 1 wherein said defibrillation electrode portion comprises a conductive portion and an insulative portion, and wherein said hydrogel layer is located substantially only on said insulative portion when dry and can expand to substantially cover said conductive portion when hydrated.

10. The lead of claim 1 and further comprising an electrolyte loaded into said hydrogel layer.

11. The lead of claim 1 and further comprising a drug loaded into said hydrogel layer.

12. The lead of claim 1 and further comprising a nonhydrogel polymer blended with said hydrogel layer.

13. The lead of claim 1 and further including a sensing electrode located proximal of said distal end and wherein said hydrogel layer at least partially covers said sensing electrode.

14. A method for extracting from tissue a chronically implanted cardiac lead having a hydrogel coating and a proximal portion comprising the steps of:
   (a) applying traction on the lead from the proximal portion; and
   (b) separating the lead from the tissue along the hydrogel coating.

15. The method of claim 14 wherein said step (b) separates most of the hydrogel coating from the rest of the lead.

16. The method of claim 14 wherein said step (b) separates most of the hydrogel coating from the tissue.

17. The method of claim 14 wherein said step (b) separates the hydrogel coating into layers, leaving a first layer of hydrogel coating attached to the lead and leaving a second layer of hydrogel coating attached to the tissue.

18. The method of claim 14 and further comprising the step of inserting a locking stylet into a lumen of the lead prior to applying traction in step (a).

19. The method of claim 14 and further comprising twisting the lead from the proximal portion to help separate the lead from the tissue.

20. The method of claim 14 and further comprising sliding an extraction sheath over the lead to help separate the lead from the tissue.

* * * * *